(12) United States Patent
Yanagawa et al.

(10) Patent No.: US 11,474,065 B2
(45) Date of Patent: Oct. 18, 2022

(54) BIOMOLECULE MEASURING DEVICE

(71) Applicant: Hitachi High-Technologies Corporation, Tokyo (JP)

(72) Inventors: Yoshimitsu Yanagawa, Tokyo (JP); Yusuke Goto, Tokyo (JP); Michiru Fujioka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 994 days.

(21) Appl. No.: 16/304,517

(22) PCT Filed: Apr. 11, 2017

(86) PCT No.: PCT/JP2017/014740
§ 371 (c)(1),
(2) Date: Nov. 26, 2018

(87) PCT Pub. No.: WO2017/208631
PCT Pub. Date: Dec. 7, 2017

(65) Prior Publication Data
US 2019/0137431 A1    May 9, 2019

(30) Foreign Application Priority Data

Jun. 3, 2016 (JP) .............................. JP2016-111688

(51) Int. Cl.
| | | |
|---|---|---|
| *C12M 1/00* | (2006.01) |
| *G01N 27/22* | (2006.01) |
| *C12Q 1/68* | (2018.01) |
| *G01N 27/00* | (2006.01) |
| *C12Q 1/6869* | (2018.01) |

(52) U.S. Cl.
CPC ............. *G01N 27/226* (2013.01); *C12M 1/00* (2013.01); *C12Q 1/68* (2013.01); *C12Q 1/6869* (2013.01); *G01N 27/00* (2013.01)

(58) Field of Classification Search
USPC .......... 435/283.1, 287.1, 287.2; 422/50, 68.1
See application file for complete search history.

(56) References Cited

U.S. PATENT DOCUMENTS

| | | |
|---|---|---|
| 2005/0202444 A1 | 9/2005 | Zhu |
| 2005/0258821 A1 | 11/2005 | Wang et al. |
| 2010/0099198 A1 | 4/2010 | Zhao et al. |
| 2015/0159213 A1 | 6/2015 | Turner et al. |

(Continued)

FOREIGN PATENT DOCUMENTS

| | | |
|---|---|---|
| JP | 2005-257687 A | 9/2005 |
| JP | 2013-535162 A | 9/2013 |

(Continued)

OTHER PUBLICATIONS

"Circuits and Phase". Printed on Nov. 18, 2018.*

(Continued)

*Primary Examiner* — Frank W Lu
(74) *Attorney, Agent, or Firm* — Crowell & Moring LLP

(57) ABSTRACT

An object of the present invention is to provide a biomolecule measuring device that can decrease the influence of crosstalk between chambers. A biomolecule measuring device according to the present invention supplies, to electrodes equipped on chambers, voltages modulated differently to each other.

10 Claims, 15 Drawing Sheets

(56) References Cited

U.S. PATENT DOCUMENTS

2017/0276678 A1\* 9/2017 Ervin ................ G01N 33/6872
2018/0217123 A1 8/2018 Goto et al.

FOREIGN PATENT DOCUMENTS

JP 2016-57263 A 4/2016
WO WO 2012/000079 A1 1/2012

OTHER PUBLICATIONS

The definition of "film". Printed on Nov. 18, 2018.\*
The definition for "Actuator" from Wikipedia. Printed on Nov. 18, 2018.\*
International Search Report (PCT/ISA/210) issued in PCT Application No. PCT/JP2017/014740 dated Jul. 18, 2017 with English translation (five (5) pages).
Japanese-language Written Opinion (PCT/ISA/237) issued in PCT Application No. PCT/JP2017/014740 dated Jul. 18, 2017 (three (3) pages).
Lathrop D. et al., "Monitoring the Escape of DNA from a Nanopore Using an Alternating Current Signal", Journal of American Chemical Society, Feb. 17, 2010, pp. 1878-1885, vol. 132, Issue No. 6, National Institute of Health, (20 pages).
Wang D. et al., "Physical Origin of Dynamic Ion Transport Features Through Single Conical Nanopores at Different Bias Frequencies", Chemical Science, 2014, pp. 1827-1832, Issue No. 5, Royal Society of Chemistry (six (6) pages).

\* cited by examiner

BIOMOLECULE MEASURING DEVICE

TECHNICAL FIELD

The present invention relates to a biomolecule measuring device.

BACKGROUND ART

Nowadays, attention is focused on a biomolecule measuring device that uses nanometer-scale micropores (in the following, referred to as nanopores) formed on a thin film as sensors. Patent Literature 1 below describes a technique in which: electrodes are provided on both sides of a nanopore, a tunneling current flowing through DNA (deoxyribonucleic acid) molecules in the nanopore is measured to identify base types. Compared with conventional fluorescence-type DNA sequencers using, the technique described in the Patent Literature 1 does not need any expensive fluorescent reagent, and does not need any DNA elongation reaction when identifying sequences. Thus, the technique is not prone to cause errors due to elongation reactions. Therefore, the technique is regarded as a promising new type of DNA sequencer that determines DNA base sequences at low costs with high accuracy and long reads. The measurement target molecules are not only DNA, of course including RNA (ribonucleic acid), but also biopolymers such as proteins, and these molecules can be evaluated with an appropriate selection of nanopore diameters.

Nanopore-type DNA sequencers can improve base encoding velocity (throughput) by the integration of nanopores and simultaneous measurement of blockade currents at the nanopores. However, the development history of nanopores is short, and the alignment of nanopores is 500 nanopores at most at the year of 2015. This is far short of a few billions done by conventional fluorescence-type DNA sequencers, and the throughput is slow by two digits or more. Therefore, it is expected that integration is further advanced in future and throughput is improved.

CITATION LIST

Patent Literature

Patent Literature 1: Japanese Unexamined Patent Application Publication No. 2005-257687

SUMMARY OF INVENTION

Technical Problem

In biomolecule measuring devices using nanopores, an increase in the integration degree of nanopores may cause the blockade current signal leakage (crosstalk) of a nanopore to the adjacent nanopore, resulting in deterioration of measurement accuracy. In order to improve throughput specifically, the distance between nanopores could be decreased, which deteriorates the impedance between nanopores and thus might make crosstalk more noticeable.

The present invention has been made in view of the circumstances. An objective of the present invention is to provide a biomolecule measuring device that can decrease the influence of crosstalk between chambers.

Solution to Problem

A biomolecule measuring device according to the present invention supplies, to electrodes equipped on chambers, voltages modulated differently to each other.

Advantageous Effects of Invention

According to the biomolecule measuring device of the present invention, even though the integration degree is increased, the influence of crosstalk can be decreased.

DESCRIPTION OF EMBODIMENTS

First Embodiment

Figure 1:
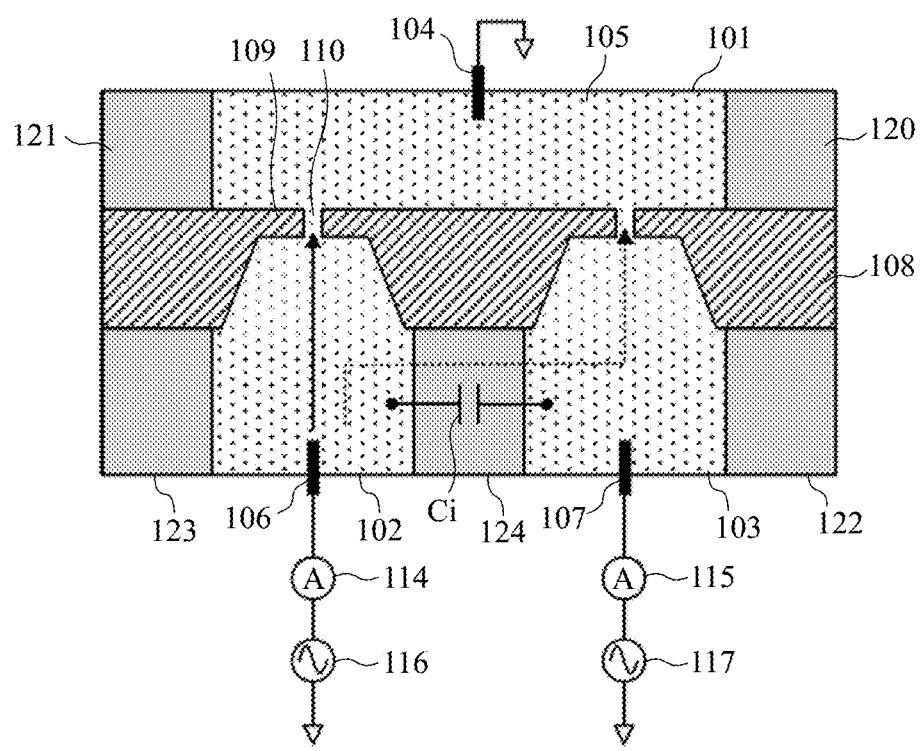
FIG. 1 is a block diagram of a biomolecule measuring device according to a first embodiment.

FIG. 1 is a block diagram of a biomolecule measuring device according to a first embodiment of the present invention. The biomolecule measuring device according to the first embodiment includes a reference chamber 101, a first chamber 102, a second chamber 103, and a nanopore chip 108. The reference chamber 101 is surrounded by partition walls 120 and 121 and the nanopore chip 108. The first chamber 102 is surrounded by partition walls 123 and 124 and the nanopore chip 108. The second chamber 103 is surrounded by a partition wall 122, the partition wall 124, and the nanopore chip 108. The chambers are filled with an electrolytic solution 105.

The reference chamber 101 has a reference electrode 104. The first chamber 102 has a first electrode 106. The second chamber 103 has a second electrode 107. The electrodes are immersed in the electrolytic solution 105.

On the nanopore chip 108, a membrane 109 is formed. On the membrane 109, nanopores 110 are formed. The reference chamber 101 communicates with the first chamber 102 through the left nanopore 110 in FIG. 1, and the reference chamber 101 communicates with the second chamber 103 through the right nanopore 110. The membrane 109 is considerably thin, and has a thickness ranging from a sub-nanometer to a few tens nanometers, for example, depending on biomolecule samples that are measurement targets. Although the diameter of the nanopore 110 depends on measurement targets, in the case in which a single-stranded DNA is read, the diameter desirably ranges on the order of approximately one nanometer to five nanometers. This is because when the diameter is smaller than approximately one nanometer, a single-stranded DNA fails to pass through the nanopore 110, whereas when the diameter is greater than five nanometers, variations of blockade currents corresponding to the differences of basic species become small, resulting in deterioration of identification accuracy.

To the first electrode 106, an ammeter 114 and a voltage source 116 are connected. To the second electrode 107, an ammeter 115 and a voltage source 117 are connected. The detail of the ammeters and the voltage sources will be described later.

Figure 2:
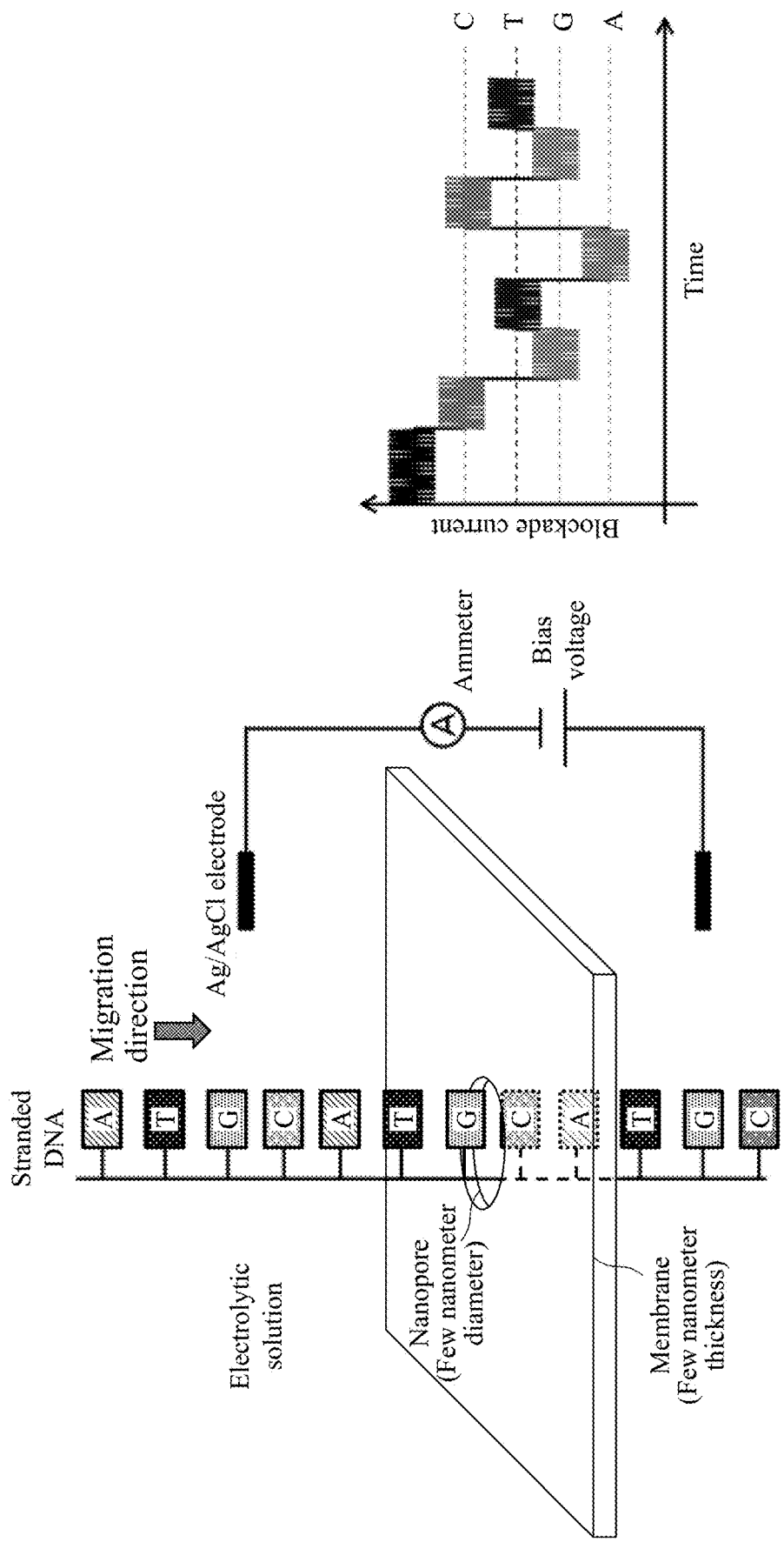
FIG. 2 is a diagram illustrating a method of measuring a blockade current.

FIG. 2 is a diagram illustrating a method of measuring a blockade current. First, a DNA sample that is a measurement target is put into the reference chamber 101. DNA is distributed into the reference chamber 101 by diffusion. At this time, when a positive voltage is applied to the first and second electrodes 106 and 107 relative to the potential of the reference electrode 104, the DNA sample is guided to the nanopore 110 due to a potential gradient formed near the nanopore 110. This is because the DNA is negatively charged. When the DNA enters the nanopore 110, the blockage ratio of the nanopore 110 is changed depending on types of bases present in the nanopore 110. At this time, when a bias voltage is applied to the first and second electrodes 106 and 107, as shown in FIG. 2, electric currents (blockade currents) corresponding to the blockage ratios of bases flow between the first electrode 106 and the reference electrode 104 and between the second electrode 107 and the reference electrode 104. Basic species in the nanopore 110 can be estimated from the values of the blockade currents at this time.

The voltage value when introducing DNA into the nanopore 110 may be different from the bias voltage value when measuring blockade currents. It is possible to measure the blockade currents by efficiently guiding DNA to the nanopore 110 at a voltage of one volt or more, for example, and by dropping the voltage to the range of approximately 100 to 500 mV after the DNA is introduced into the nanopore 110. By dropping the bias voltage after the DNA is introduced into the nanopore 110, the electric fields near the nanopore 110 are weakened to slow the velocity of the advancing DNA. Consequently, since the number of samples for measuring blockage signals per base can be increased without changing the ammeter 114 or 115, this exerts the advantage of improving accuracy.

Crosstalk in the measurement of blockage signals will be described below. In FIG. 1, the first chamber 102 is adjacent to the second chamber 103 through the partition wall 124. In the following, for convenience of explanation, the system that measures blockade currents with the first chamber 102, the first electrode 106, the ammeter 114, and the voltage source 116 is referred to as ch1, and the system that measures blockade currents with the second chamber 103, the second electrode 107, the ammeter 115, and the voltage source 117 is referred to as ch2. The partition wall 124 is formed of an insulating material, such as a resin, and hence crosstalk due to a leakage current like a direct current between ch1 and ch2 can be reduced. On the other hand, since a parasitic capacitance Ci is present between the first chamber 102 and the second chamber 103, the parasitic capacitance Ci causes a state in which the first chamber 102 is coupled to the second chamber 103 in terms of alternating current, and this might cause crosstalk.

Figure 3:
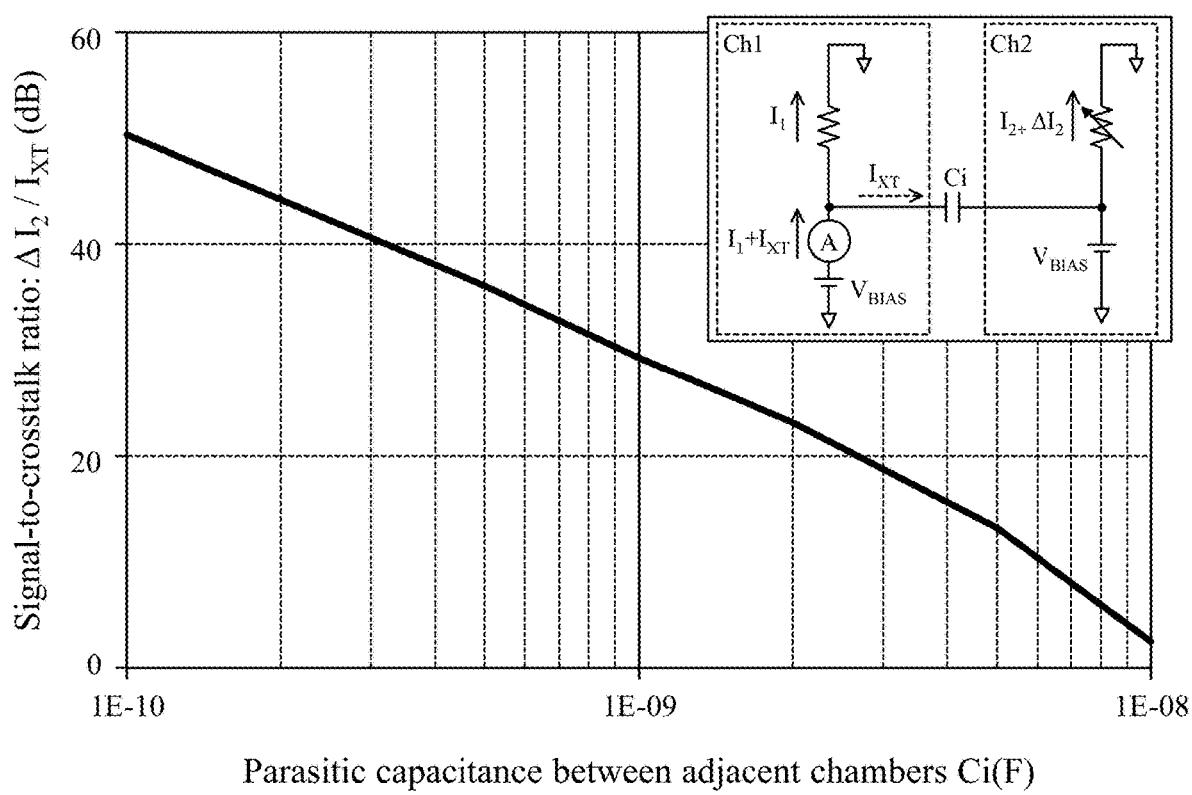
FIG. 3 shows the result that when a blockade current is changed by $\Delta I_2$ for 100 µs at ch2, a crosstalk amount $I_{XT}$ leaked into ch1 through a parasitic capacitance Ci is evaluated by simulation.

FIG. 3 shows the result that a crosstalk amount $I_{XT}$ leaked into ch1 through the parasitic capacitance Ci is evaluated by simulation when a blockade current is changed by $\Delta I_2$ for 100 μs at ch2. The horizontal axis expresses the capacitance of the parasitic capacitance Ci. The vertical axis expresses the ratio of $\Delta I_2$ to the crosstalk amount $I_{XT}$ of blockage signals, showing the level of signal quality. In this case, when Ci is approximately one nanofarad, the signal amount is 32 dB, and quality is sufficiently obtained. However, when Ci is ten nanofarads, the signal amount is dropped down to 0 dB, i.e. this means the the crosstalk amount $I_{XT}$ deteriorates to almost the same level as the blockage signal amount $\Delta I_2$. Decreasing the thickness of the partition wall 124 is effective for high integration of the nanopores 110. However, this causes an increase in Ci, resulting in an increase in crosstalk. In order to keep the measurement quality of blockade currents even when a nanopore array is highly integrated, the crosstalk amount has to be decreased.

Figure 4:
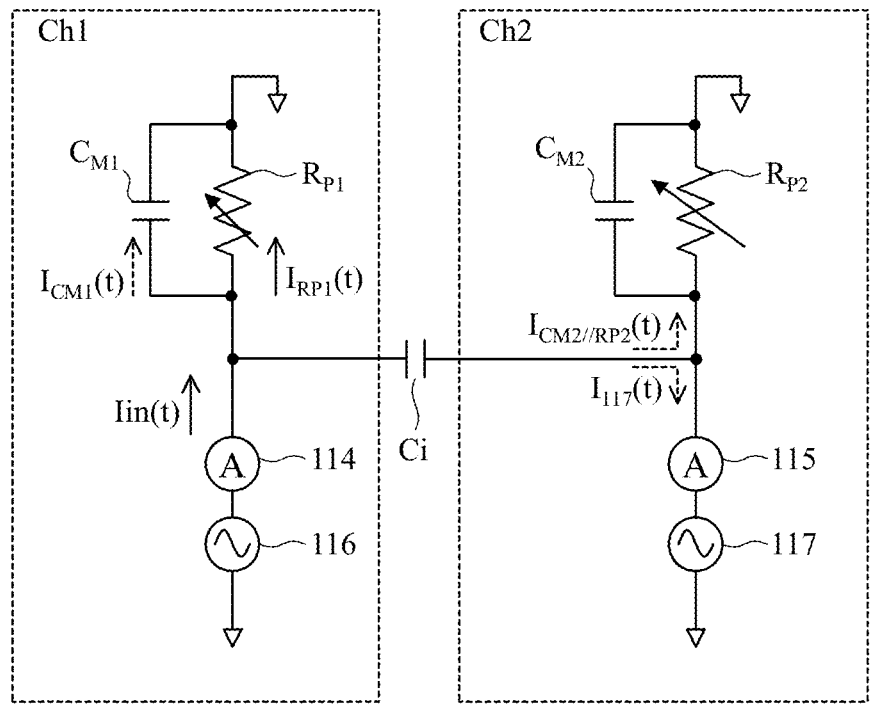
FIG. 4 is a diagram of an equivalent circuit of the circuit in FIG. 1.

FIG. 4 is a diagram of an equivalent circuit of the circuit in FIG. 1. It can be considered that when the nanopore 110 is blocked by DNA, the resistance value of the nanopore 110 is changed. Therefore, in FIG. 4, the nanopore 110 is expressed as variable resistors $R_{P1}$ and $R_{P2}$ that change correspondingly to blocking amounts. $C_{M1}$ and $C_{M2}$ are parasitic capacitances of the membrane 109 or the nanopore chip 108; the former corresponds to the first chamber 102, and the latter corresponds to the second chamber 103.

Figure 5:
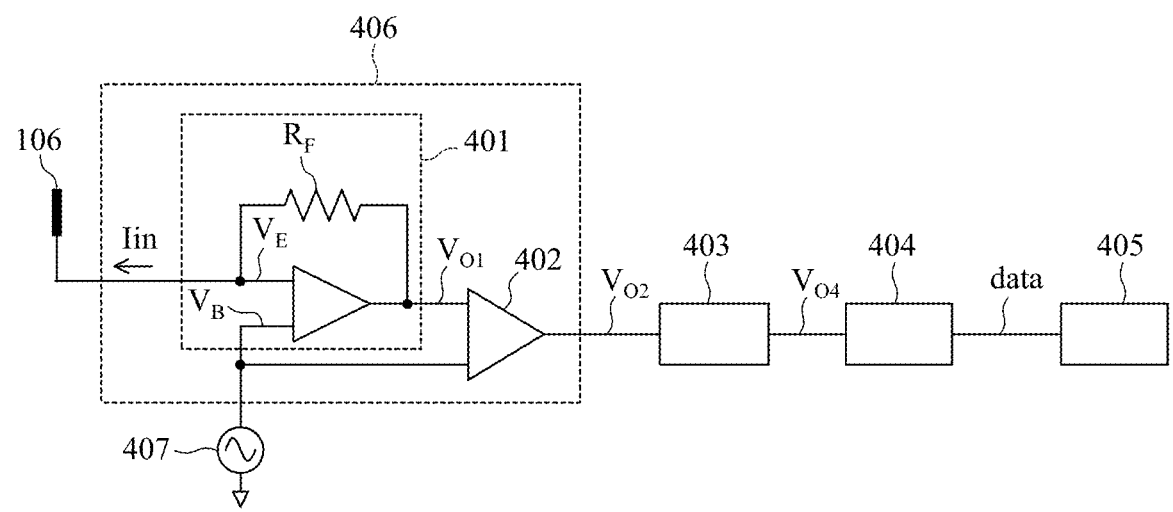
FIG. 5 is a specific exemplary configuration of a voltage source 116 and an ammeter 114 for one channel.

FIG. 5 is a specific exemplary configuration of the voltage source 116 and the ammeter 114 for one channel. A circuit composed of an amplifier circuit 406 and a voltage source 407 in FIG. 5 corresponds to a circuit integrally composed of the voltage source 116 and the ammeter 114. An arithmetic logic unit 405 acquires a result measured by the ammeter 114 through a filter circuit 403 and an AD converter 404 for processing. The filter circuit 403, the AD converter 404, and the arithmetic logic unit 405 may be included as the components of the biomolecule measuring device, or may be constructed separately. The arithmetic logic unit 405 can be constructed using a computer including a CPU (Central Processing Unit), for example. However, suitable arithmetic operation devices may be used other than the computer.

A trans-impedance amplifier 401 converts a blockade current $I_{in}$ carried through the first electrode 106 into a voltage signal. To the reference terminal of the trans-impedance amplifier 401, a modulated bias voltage $V_B$ is applied from the voltage source 407. Since the trans-impedance amplifier 401 operates so as to equalize the bias voltage $V_B$ applied to the reference terminal with a voltage $V_E$ at an electric current input terminal, the voltage $V_E$ is also modulated correspondingly to the bias voltage $V_B$. The blockade current $I_{in}$ at this time is expressed by Equation 1 below with the equivalent resistance $R_P$ of the nanopore 110. The modulation method of the bias voltage $V_B$ is non-limiting. However, here, $V_E = V_0 * \sin(\omega t)$, assuming a simple sine wave where w is an angular frequency.

[Eq. 1]

$$I_{in}(t) = \frac{V_E}{R_P} = \frac{V_0 \sin(\omega t)}{R_P} \quad (1)$$

Figure 6:
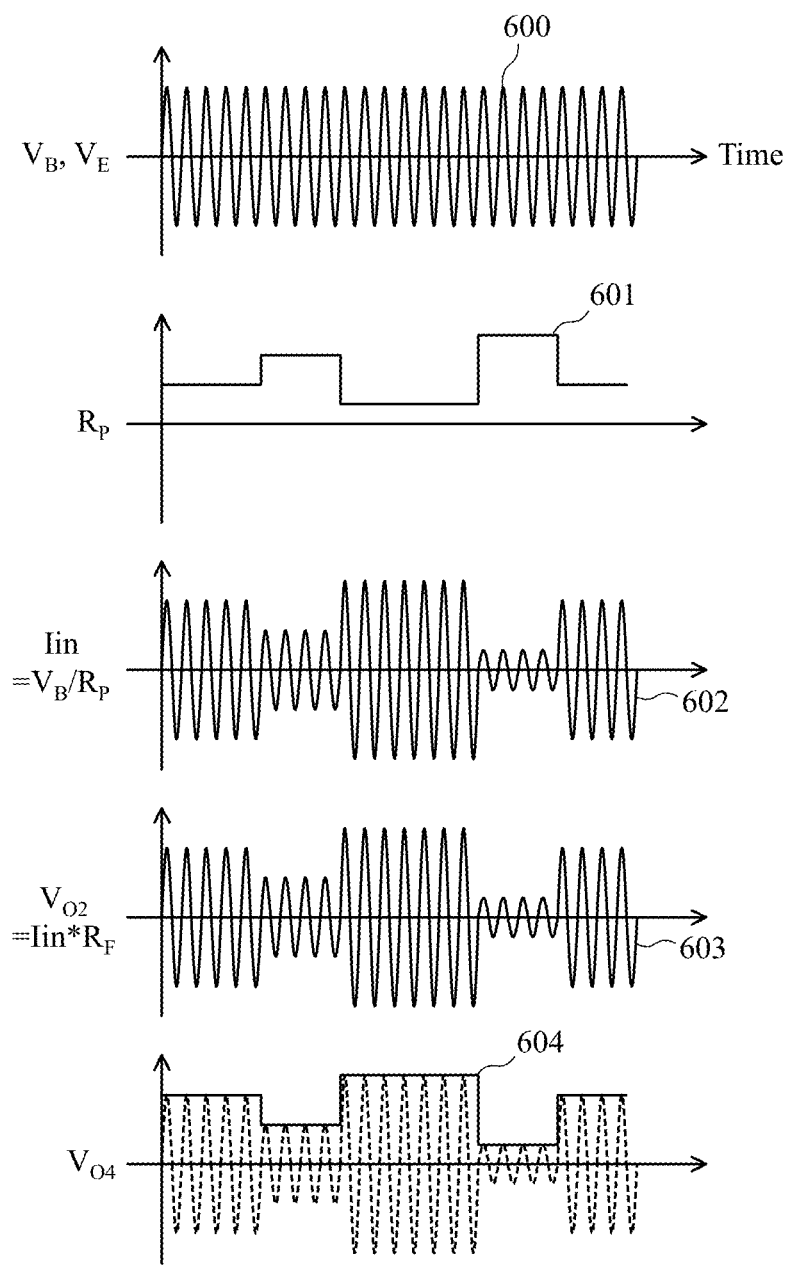
FIG. 6 is a waveform diagram of signals.

FIG. 6 is waveform diagrams of signals. When the blockage ratio of the nanopore 110 is changed, $R_p$ is changed. As a result, $I_{in}(t)$ of Equation 1 is an amplitude-modulated sine wave due to a change in $R_p$. A waveform 600 is the voltage waveform of the bias voltage $V_B$ and the voltage $V_E$. Suppose that DNA translocation in the nanopore 110 causes a change in the blockage ratio and the equivalent resistance $R_P$ changes as a waveform 601, the blockade current $I_{in}$ is an amplitude-modulated waveform as a waveform 602. An output $V_{O1}$ of the trans-impedance amplifier 401 is $I_{in}*R_F + V_E$. The differential amplifier 402 subtracts the $V_E$ component, and hence output $V_{O2} = I_{in}*R_F$ shown in a waveform 603 is obtained. The filter circuit 403 demodulates the amplitude of $V_{O2}$, and then an output waveform 604 is acquired in which the waveform 601 is amplified. The filter circuit 403 may be a classic envelope detection circuit simply composed of a diode, a resistor, and a capacitor, or synchronous detection may be performed by a lock-in amplifier, described later.

Now it is assumed that, sine waves at frequencies $\omega_1$ and $\omega_2$ different from each other as the bias voltage $V_B$ are applied to ch1 and ch2 respectively. At this time, the electric current component $I_{in}(t)$ inputted to the ammeter 114 is expressed by Equation 2 and Equation 3 below.

[Eq. 2]

$$I_{in}(t) = I_{RP1}(t) + I_{CM1}(t) + I_{CM2//RP2}(t) + I_{117}(t) \quad (2)$$
$$= \frac{V_0 \sin(\omega_1 t)}{R_{P1}} + \frac{V_0 \sin(\omega_1 t)}{\frac{1}{j\omega_1 C_{M1}}} + \frac{V_0 \sin(\omega_1 t)}{R_{P2} + \frac{1}{j\omega_1 C_{M2}}} + \frac{1}{j\omega_1 C_i} +$$
$$\frac{V_0 \sin(\omega_1 t) - V_0 \sin(\omega_2 t)}{\frac{1}{j\omega_1 C_i}}$$

[Eq. 3]

$$\Phi_{CM2//RP2} = -\arctan\left(\frac{\omega^2 C_{M2}^2 R_{P2}^2 + \omega^2 C_{M2} C_i R_{P2} + 1}{\omega R_{P2} C_i}\right) \quad (3)$$

$I_{RP1}$ is an electric current component flowing through the resistor $R_{P1}$, and is a desired blockade current signal. Since $I_{RP1}$ is a resistance component, $I_{RP1}$ changes in the same phase at the same frequency to the bias voltage $V_B$. $I_{CM1}$ is an electric current component flowing through the parasitic capacitance $C_{M1}$ having the same frequency as the bias voltage $V_B$ but having a phase that is rotated by 90° from that of the bias voltage $V_B$. $I_{CM2//RP2}$ is an electric current component flowing in parallel with the capacitance $C_{M2}$ and the resistor $R_{P2}$ through the parasitic capacitance $C_i$ between ch1 and ch2. The frequency of $I_{CM2//RP2}$ is $\omega_1$ and equal to the frequency of $I_{RP1}$, but its phase rotates due to the influence of the capacitances Ci and $C_{M2}$. $\Phi_{CM2//RP2}$ is the rotation angle of this phase. $I_{117}$ is an electric current component flowing into the voltage source 117, and has a phase and a frequency different from those of the bias voltage $V_B$. The description above shows that the components other than $I_{RP1}$ have phases and frequencies different from those of the bias voltage $V_B$. Therefore, synchronous detection is performed on the obtained electric current $I_{in}$ using the bias voltage $V_B$ as a reference signal, and hence the frequency and the phase are selectively detected to extract only $I_{RP1}$.

Figure 7:
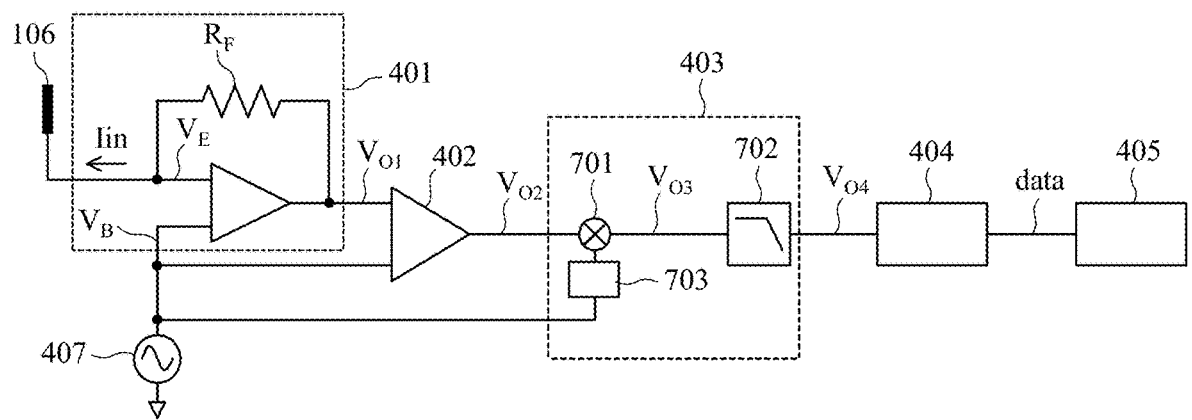
FIG. 7 is an example using a lock-in amplifier as a filter circuit 403.

FIG. 7 is an example using a lock-in amplifier as the filter circuit 403. The lock-in amplifier is an example of a synchronous detection circuit. The analog mixer 701 multiplies the signal of a measurement target by the reference signal. The filter 702 extracts the DC component of the signal. A phase shifter 703 that finely tunes the phase of the reference signal may be included, as necessary. In the first embodiment, the bias voltage $V_B$ inputted to the trans-impedance amplifier 401 is inputted as a reference signal. Thus, the lock-in amplifier can accurately extract a component alone having a frequency and a phase matched with the frequency and the phase of the first term on the right-hand side of Equation 2.

Synchronous detection is not necessarily implemented by a circuit. For example, as shown in FIG. 5, synchronous detection may be possible by converting a measured result into a digital signal by the AD converter 404, and by performing data processing to the measured result to extract $I_{RP1}$ by the arithmetic logic unit 405. Thus, an increase in the circuit scale can be prevented even when the integration degree is improved. Even in the case in which synchronous detection is performed without using any circuit, the filter circuit 403 may be included. When the filter circuit 403 is a low-pass filter, the circuit 403 prevents aliasing in the AD converter 404 and can remove noise that is present out of a desired band in advance. Consequently, the signal quality can be improved further.

Figure 8:
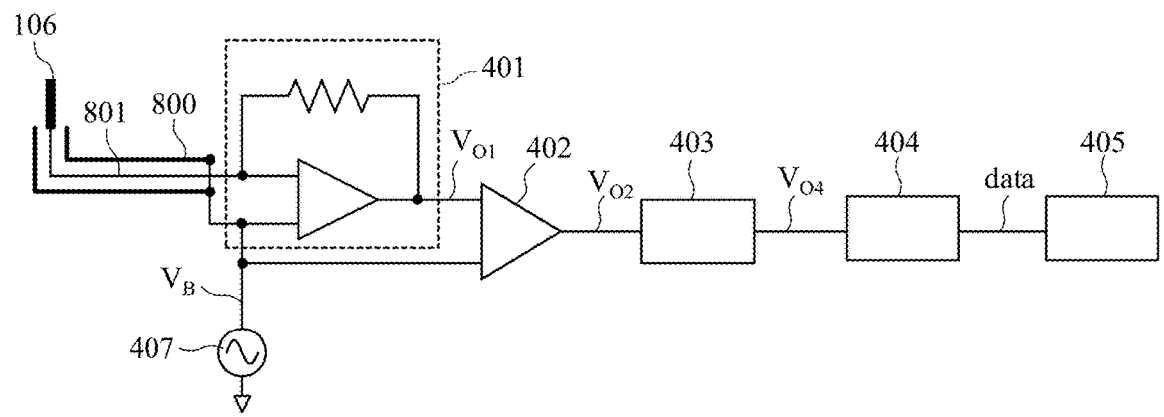
FIG. 8 is an exemplary modification of the first embodiment.

FIG. 8 is an exemplary modification of the first embodiment. In FIG. 8, in addition to the configuration described in FIG. 5, a guard electrode 800 is disposed in parallel with a wire 801 on a path from the electric current input terminal of the trans-impedance amplifier 401 to the first electrode 106. The guard electrode 800 is connected to the voltage source 407. Thus, since the potentials of the wire 801 and the guard electrode 800 are kept at the same potential, an electric current leaking from the wire 801 to the neighboring components is decreased, and a blockade current can be more highly accurately measured. This configuration is specifically effective in the case in which the impedance of the nanopore 110 is high and an electric current leaking from the wire 801 to the neighboring circuits is unignorable compared with a blockade current. Also for the second electrode 107, the guard electrode can be similarly provided.

Figure 9:
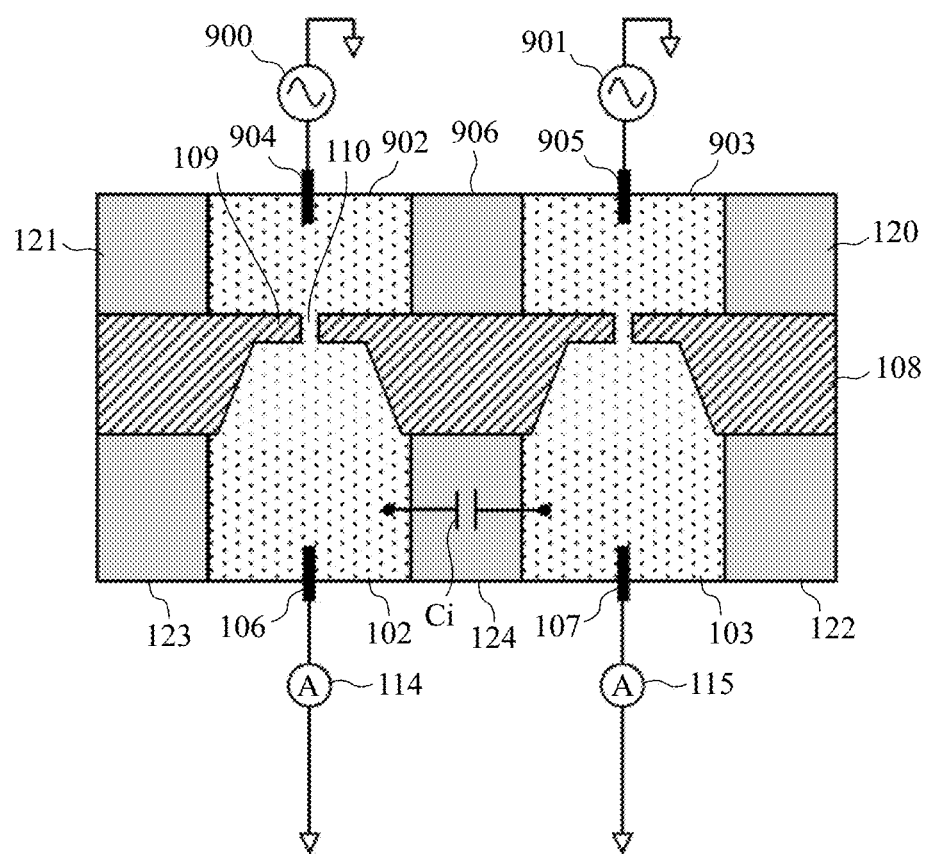
FIG. 9 is an exemplary modification of the first embodiment.

FIG. 9 is an exemplary modification of the first embodiment. In FIG. 9, the reference chamber 101 is isolated by a partition wall 906. The reference electrode 104 is isolated as two separate electrodes 904 and 905. This isolates, between the adjacent channels, the DC path through which the blockade current flows. In addition, voltage sources 900 and 901 (corresponding to the voltage sources 116 and 117) are respectively connected to the separate electrodes 904 and 905, and no voltage source is connected to the ammeters 114 and 115. In this configuration, the voltage source connected to the trans-impedance amplifier 401 is on the electric current input terminal side. The potential inputted to the reference terminal may be a reference potential such as GND, for example. Thus, the trans-impedance amplifier 401 operates so as to match the output with the reference potential. Since the output of the trans-impedance amplifier 401 in FIG. 5 is the addition of the voltage $V_E$ and the bias voltage $V_B$, the differential amplifier 402 that subtracts the bias voltage $V_B$ is necessary. On the other hand, since the output of the trans-impedance amplifier 401 in FIG. 9 has no superposed bias voltage $V_B$, the differential amplifier 402 is eliminated to simplify the circuit.

Second Embodiment

Figure 10:
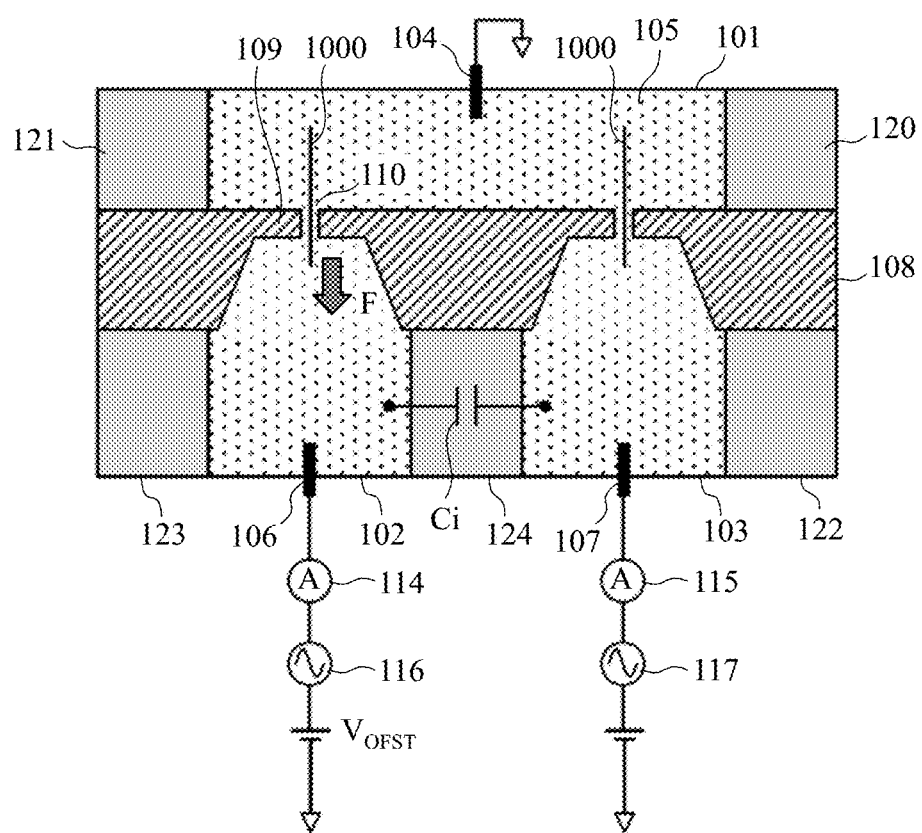
FIG. 10 is a block diagram of a biomolecule measuring device according to a second embodiment.

FIG. 10 is a block diagram of a biomolecule measuring device according to a second embodiment of the present invention. The biomolecule measuring device according to the second embodiment further includes a DC voltage source $V_{OFST}$ that offsets the bias voltage, in addition to the configuration described in the first embodiment. The DC voltage source $V_{OFST}$ acts to offset the center voltages of voltages that are supplied from voltage sources 116 and 117 from the potential of a reference electrode 104.

As the nature of DNA, it is known that at a frequency (e.g. 100 Hz or less) at which an external electric field changes, DNA moves following a change in the external electric field, whereas at high frequencies (e.g. 10 kHz to 10 MHz), DNA itself does not respond to the electric field and stops moving (e.g. Nonpatent Literature: "Conformation dependent non-linear impedance response of DNA in nanofluidic device", Pungetmongkol, et al., Proc. IEEE Internationla conference on Nanotechnology, 2015). In addition to that, since DNA is polarized in a high frequency range, DNA has a nature that DNA is linearly stretched due to an interaction with the external electric field. Therefore, the modulation frequency is set at a frequency that is faster than the response frequency of DNA and at which ions in a solution can respond or less, and hence the blockade current can be measured while DNA is linearly stretched.

A problem of nanopores is the possibility that an effective molecule diameter is increased due to entangled DNA strands or self-organized DNA, thereby the nanopore is blocked, deteriorating the measurement accuracy of a blockade current. Since modulation at the above-described frequency band obtains a linear strand of DNA, there is a merit that reduces the possibility of deteriorated measurement accuracy due to blocked nanopores. In order to acquire sequences of DNA, DNA is desirably translocated in a nanopore at a constant velocity. According to the second embodiment, DNA can be translocated at a constant velocity, and the signal quality of the blockade current can be improved. In the case in which no DC voltage source $V_{OFST}$ is present, a potential difference is generated across the reference electrode 104 and the first electrode 106, for example, and hence DNA can be translocated.

Figure 11:
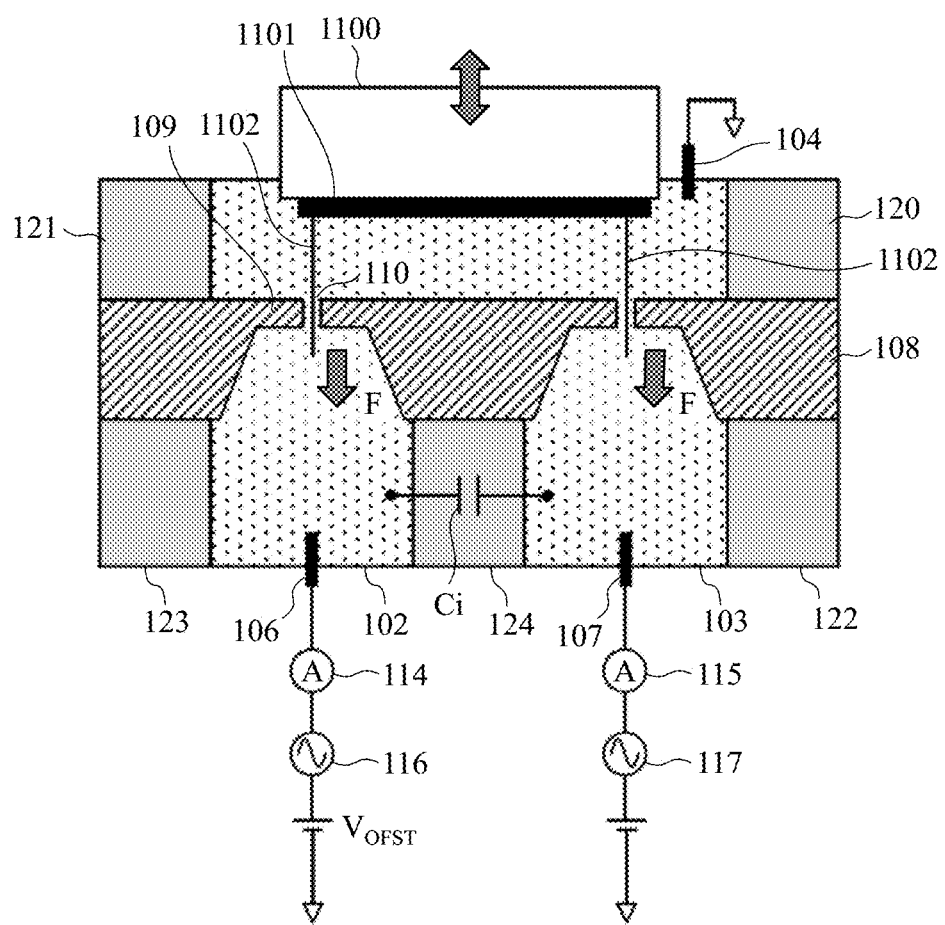
FIG. 11 is an exemplary modification of the second embodiment.

FIG. 11 is an exemplary modification of the second embodiment. A biomolecule measuring device shown in FIG. 11 translocates DNA by an actuator 1100. The actuator 1100 is preferably an actuator that can control a DNA sample in a position resolution of one nanometer or less. For example, an actuator using a piezoelectric element is appropriate for the actuator 1100. To the tip end of the actuator 1100, a substrate 1101 that is modified to immobilize DNA is connected. A DNA sample 1102 that is a measurement target is immobilized on the substrate 1101.

A DNA base sequence determination method in the exemplary modification is as follows. First, the actuator 1100 is driven in the direction where the actuator 1100 comes close to the nanopore 110, and the tip end of the DNA sample 1102 is brought close to the nanopore 110. When bringing the tip end close to the nanopore 110, the application of a positive voltage to the first electrode 106 by the offset voltage source $V_{OFST}$ based on the reference electrode 104 guides the DNA sample 1102 into the nanopore 110 by electric fields near the nanopore 110. Whether the DNA sample 1102 has entered the nanopore 110 can be confirmed by a decrease in the blockade current. Subsequently, a modulated bias voltage is applied to measure a change in the blockade current while the actuator 1100 is driven in the direction where the actuator 1100 is brought apart from the substrate 1101, thereby a base sequence pattern is determined. Also in this period, a positive voltage is desirably applied by the offset voltage source $V_{OFST}$ based on the reference electrode 104. According to such a configuration, an effect can be expected that in encoding the base sequence pattern, tension F is applied to the DNA sample 1102 in the direction toward the first electrode 106 to linearly stretch the DNA sample 1102. Thus, the DNA sample 1102 can be stably translocated, and the measurement accuracy of the blockade current can be improved.

Third Embodiment

Figure 12:
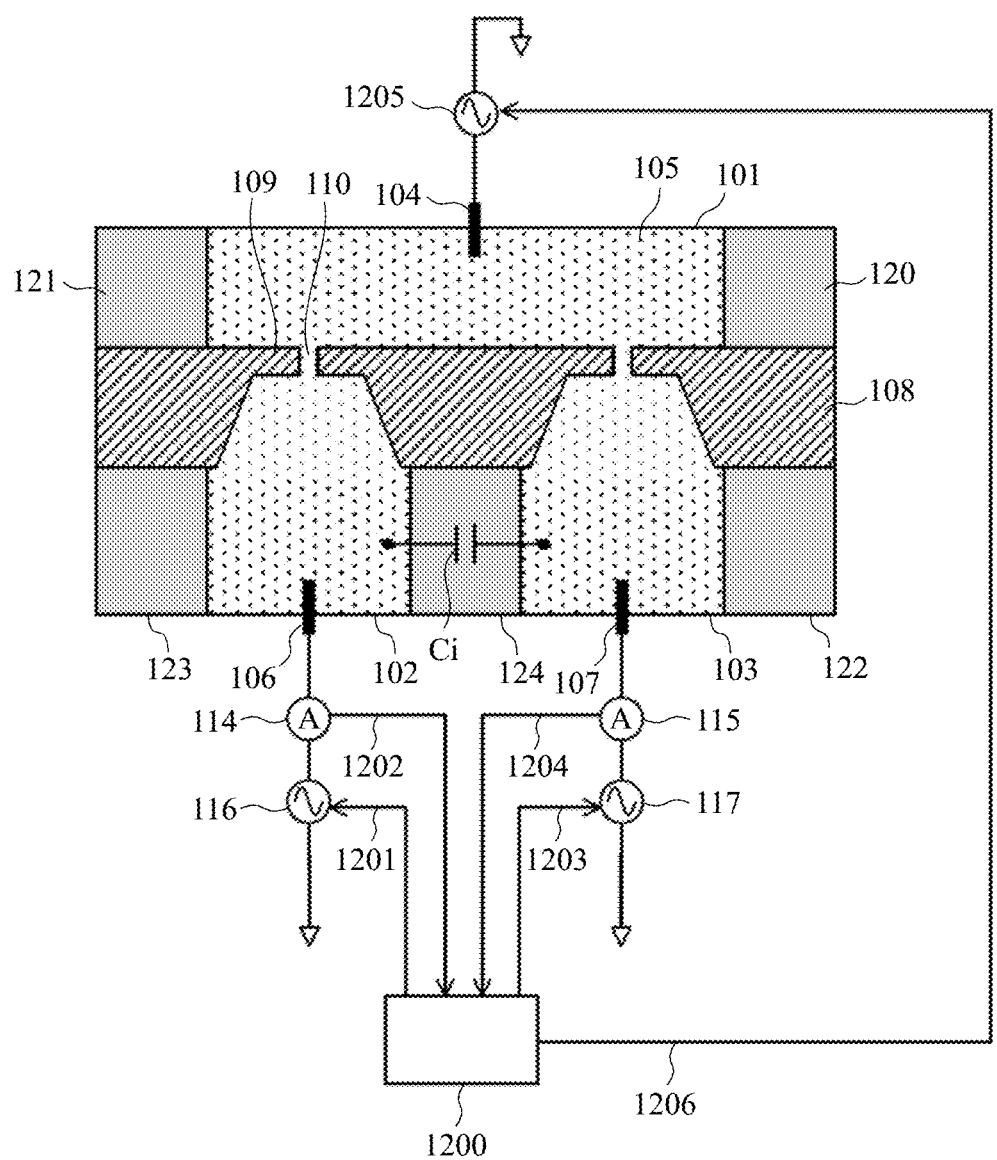
FIG. 12 is a block diagram of a biomolecule measuring device according to a third embodiment.

FIG. 12 is a block diagram of a biomolecule measuring device according to a third embodiment of the present invention. The biomolecule measuring device according to the third embodiment further includes a calibration circuit 1200 and a voltage source 1205 in addition to the components described in the first embodiment. In the third embodiment, the output signals of voltage sources 116, 117, and 1205 are controlled while the values of ammeters 114 and 115 are monitored by the calibration circuit 1200 before a DNA sample is put. Thus, parasitic capacitance components including Ci can be calculated.

Specifically, when the voltage source 117 is fixed to a reference voltage and the voltage sources 1205 and 116 are driven at the same signals (the same frequency, the same amplitude, and the same phase), the electric current measured by the ammeter 114 is the electric current component flowing through Ci. Ci can be calculated from the drive frequency/the drive amplitude/the electric current amount at this time. Similarly, when the voltage source 1205 is fixed to the reference voltage and the voltage sources 116 and 117 are driven at the same signals, the parasitic capacitance $C_{M1}$ at ch1 can be calculated based on the electric current measured by the ammeter 114. The same thing is also applied to the parasitic capacitance $C_{M2}$.

The arithmetic logic unit 405 can calculate the parasitic capacitances Ci, $C_{M1}$, and $C_{M2}$ in advance. The arithmetic logic unit 405 uses Equations 2 and 3 for the measured results by the ammeter 114, and hence can calculate a component corresponding to $I_{RP1}$ in $I_{in}(t)$. In this case, the synchronous detection circuit that extracts $I_{RP1}$ from $I_{in}(t)$ does not have to be employed. The measured results by the ammeter 114 only have to be subjected to AD conversion and delivered to the arithmetic logic unit 405 with no change. Thus, this advantageously enables a simple circuit configuration.

Figure 13:
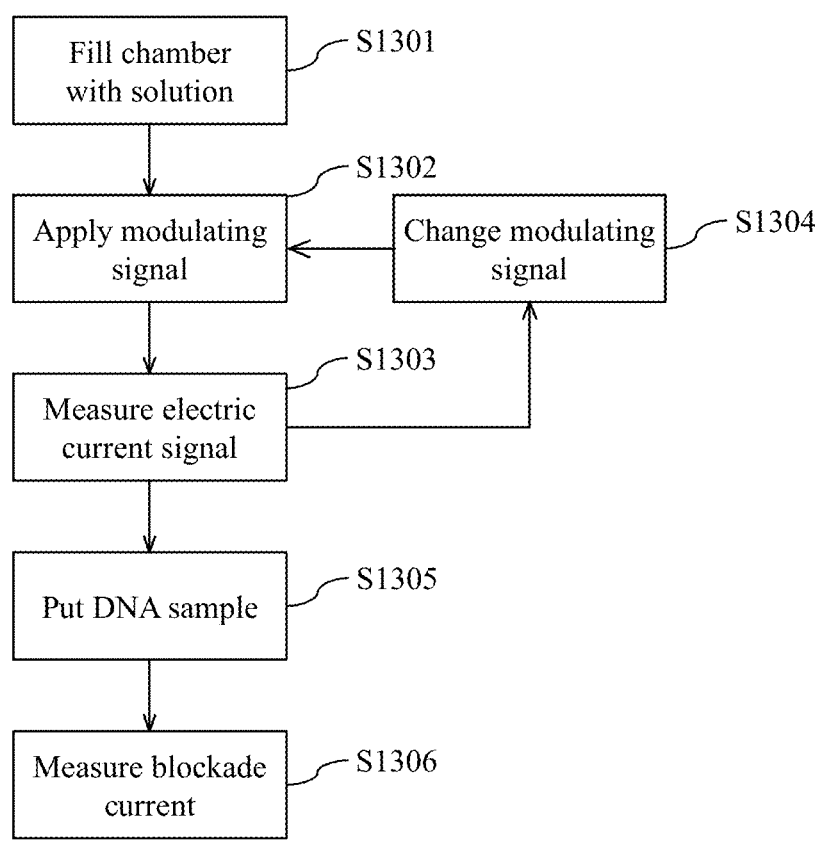
FIG. 13 is a diagram of the procedures that an arithmetic logic unit 405 determines a parasitic capacitance.

FIG. 13 is a diagram of the procedures that the arithmetic logic unit 405 determines a parasitic capacitance. First, a user puts a solution into the chambers (S1301). After that, the calibration circuit 1200 sets the potential difference between the electrodes as described above, and a modulating signal is applied from the voltage sources (S1302). The ammeters measure electric current signals, and the arithmetic logic unit 405 calculates the parasitic capacitances based on the results (S1303). Similar processes may be repeated in order to improve accuracy (S1304). After the calculation of the parasitic capacitances is finished, a DNA sample is introduced into the chambers (S1305), and blockade currents are measured (S1306). According to the procedures, various parasitic components formed due to the contact with the electrolytic solution can be accurately calculated as well as the influence of a change in the blockade current in association with putting the DNA sample can be reduced, and hence the measurement accuracy of the blockade current can be improved.

Fourth Embodiment

Figure 14:
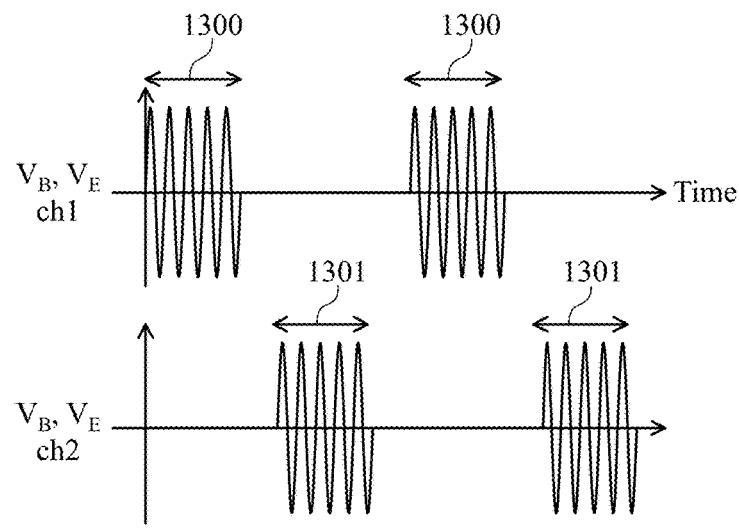
FIG. 14 is a waveform diagram illustrating the timing of applying a bias voltage in a biomolecule measuring device according to a fourth embodiment.

FIG. 14 is a waveform diagram illustrating the timing of applying a bias voltage in a biomolecule measuring device according to a fourth embodiment of the present invention. In the fourth embodiment, a bias voltage $V_B$ is temporally divided between ch1 and ch2, and intermittently applied.

Figure 15:
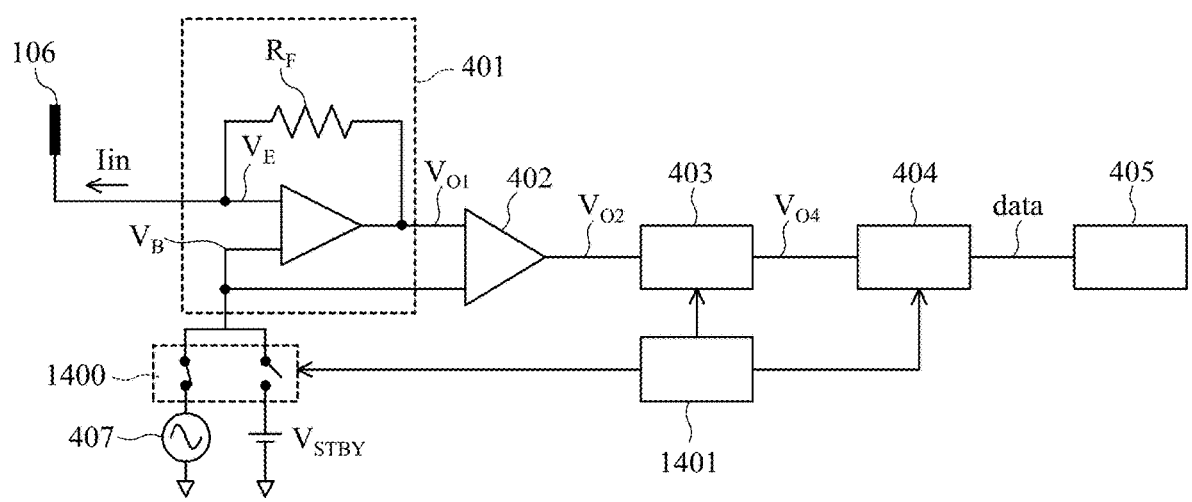
FIG. 15 is an exemplary configuration of a voltage source 116 and an ammeter 114 for one channel according to the fourth embodiment.

FIG. 15 is an exemplary configuration of the voltage source 116 and the ammeter 114 for one channel according to the fourth embodiment. The circuit configuration shown in FIG. 15 further includes a stand-by voltage power supply $V_{STBY}$, a bias voltage selection switch 1400, and a drive timing control circuit 1401 in addition to the components described in the first embodiment. In a period 1300 in FIG. 14, the bias voltage $V_B$ is applied to ch1. In the period 1300, the bias voltage $V_B$ at ch2 is fixed to a stand-by voltage $V_{STBY}$. In the period 1301, ch1 is switched to ch2. According to such a configuration, since the blockade current between the adjacent channels is isolated on the time base, crosstalk can be further decreased.

In the measurement of the blockade current, since a high electric field is applied near the nanopore, a continuous application of a bias for a long time might increase the pore diameter. In the fourth embodiment, the intermittent driving of the bias voltage $V_B$ can decrease time for which a voltage is applied to the nanopore 110, and hence the life of the nanopore 110 can be prolonged.

The timing of activating an AD converter 404 by the drive timing control circuit 1401 may be synchronized with the timing of applying the bias voltage $V_B$. According to such a configuration, the time for activating the AD converter 404 is a minimum necessary amount, and hence the power consumption of the device can be reduced. Similarly, the synchronization of the timing of activating the filter circuit 403 also with the timing of applying the bias voltage $V_B$ can further reduce power consumption.

Fifth Embodiment

Figure 16:
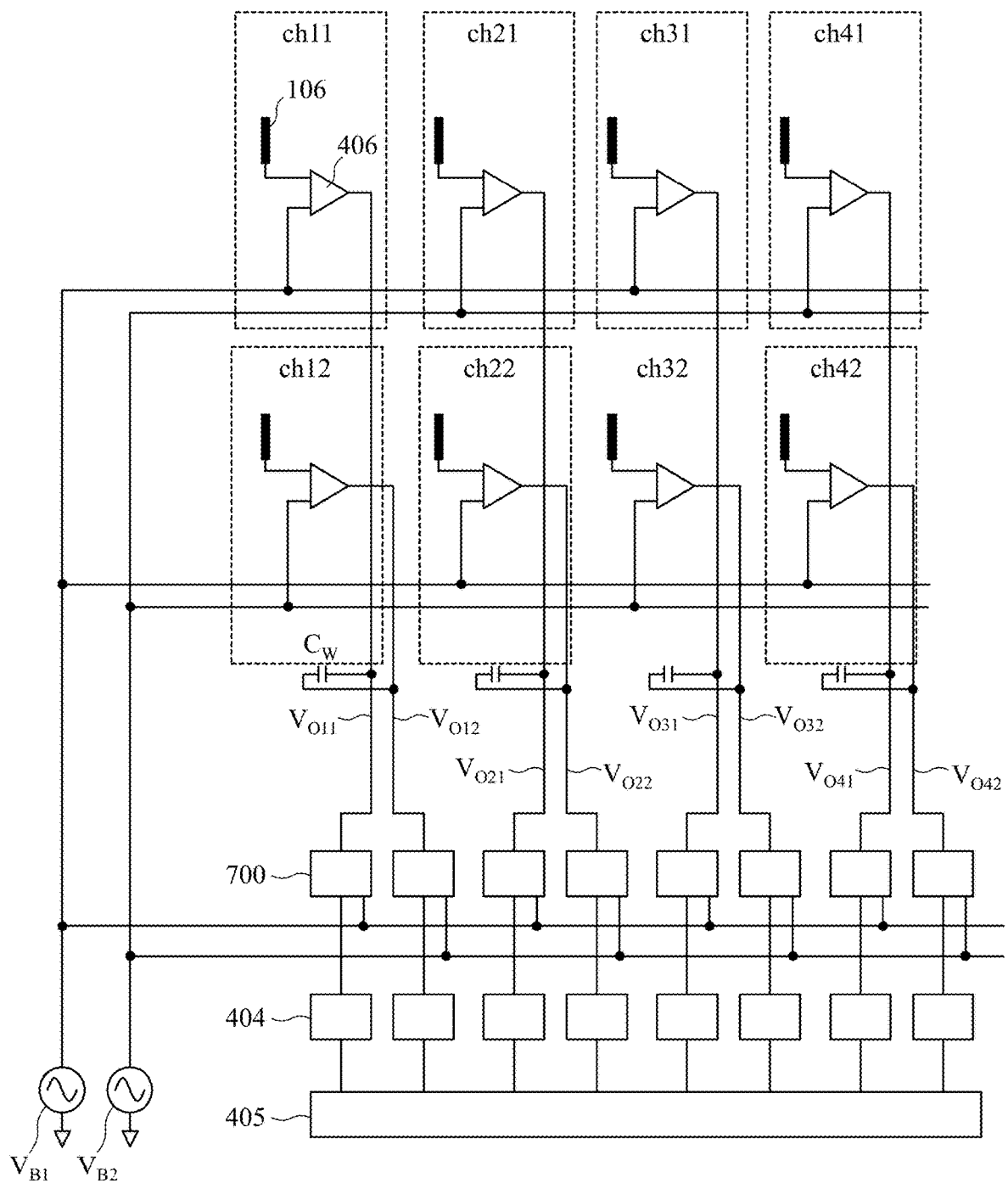
FIG. 16 is a block diagram of a biomolecule measuring device according to a fifth embodiment.

FIG. 16 is a block diagram of a biomolecule measuring device according to a fifth embodiment of the present invention. In the fifth embodiment, a plurality of amplifier circuits 406 described in the first embodiment is provided and disposed in an array configuration, and power supplies $V_{B1}$ and $V_{B2}$ are provided as the voltage sources of the amplifier circuits 406. A different bias power supply is used for the adjacent amplifier circuit 406. In the example shown in FIG. 16, the power supply $V_{B1}$ biases ch11, and the power supply $V_{B2}$ biases ch21 that is horizontally adjacent to ch11 and ch12 that is vertically adjacent to ch11. When the outputs of $V_{B1}$ and $V_{B2}$ are sine waves at different frequencies, the crosstalk between the adjacent channels with the largest parasitic capacitance can be reduced.

When the amplifier circuits 406 are disposed in an array configuration, a parasitic capacitance $C_W$ is present between the output signal wires of the channels, which becomes a factor that causes crosstalk between outputs. In the fifth embodiment, the output between the adjacent channels has different modulation. Thus, $V_{O11}$ and $V_{O12}$, for example, are demodulated at a lock-in amplifier 700 in the subsequent stage using modulated waves $V_{B1}$ and $V_{B2}$ as reference signals, and hence the outputs can be easily isolated. The bias voltage sources $V_{B1}$ and $V_{B2}$ are shared by the individual channels, and hence a necessary hardware amount can be decreased.

Sixth Embodiment

Figure 17:
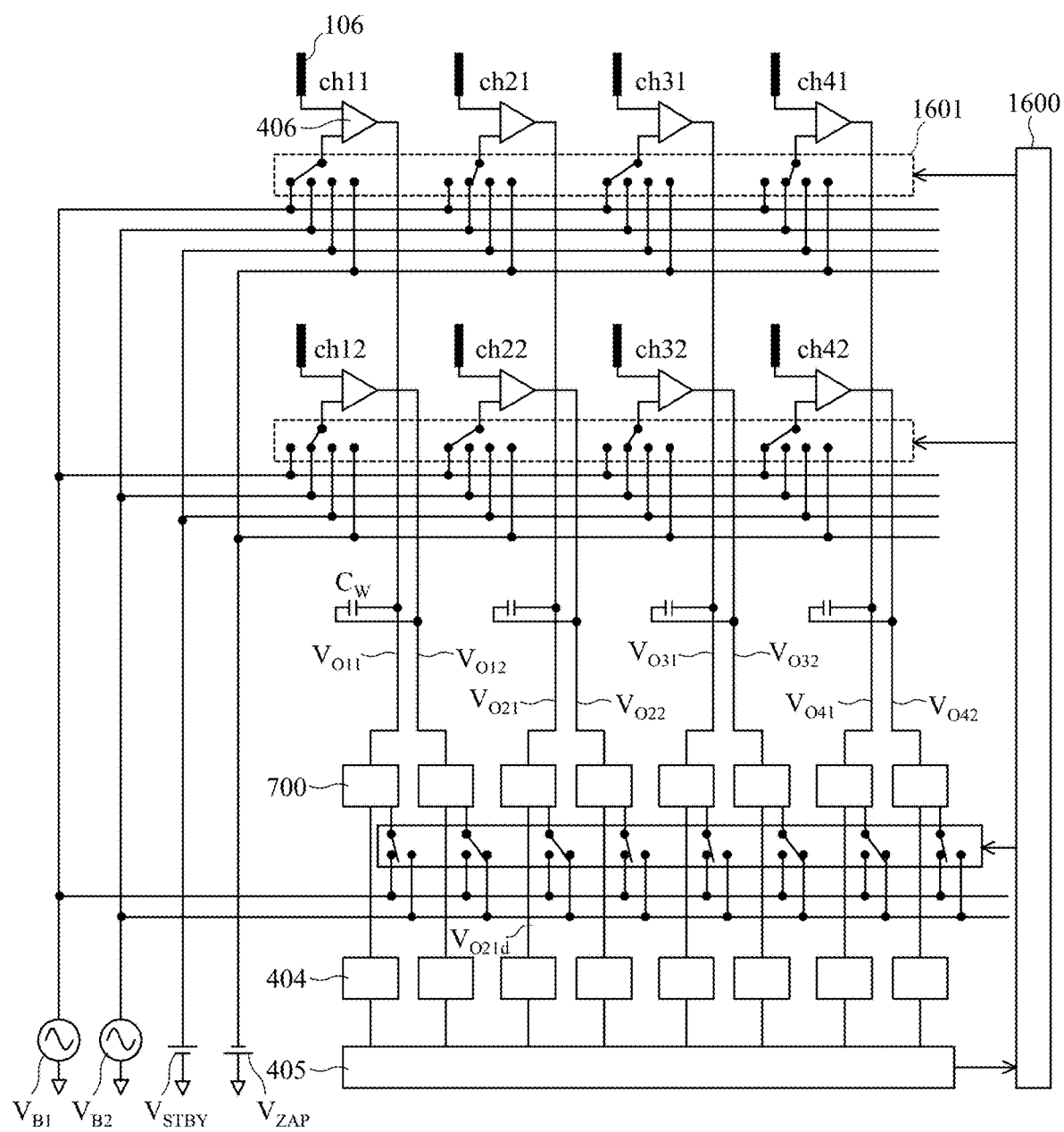
FIG. 17 is a block diagram of a biomolecule measuring device according to a sixth embodiment.

FIG. 17 is a block diagram of a biomolecule measuring device according to a sixth embodiment of the present invention. In the sixth embodiment, a plurality of amplifier circuits 406 described in the first embodiment is provided and disposed in an array configuration, and four power supplies $V_{B1}$, $V_{B2}$, $V_{STBY}$, and $V_{ZAP}$ are provided as the voltage sources of the amplifier circuits 406. The device further includes a switch 1601 that selects the bias power supply connected to the array for each channel. The device further includes a control circuit 1600 for the switches 1601.

Similarly to the fifth embodiment, in the measurement of the blockade current, different bias signals $V_{B1}$ and $V_{B2}$ are applied to the adjacent channels, and hence a high isolation performance between the channels is provided. On the other hand, a nanopore 110 is sometimes blocked in the translocation of DNA. Once the nanopore 110 is blocked, the encoding of the subsequent base sequence later is not enabled. Thus, in the case in which the nanopore 110 is blocked, the blocking has to be eliminated any time. In the sixth embodiment, a negative voltage $V_{ZAP}$ is selectively applied to the nanopore 110 that has been blocked, a force in the direction reverse to the translocation direction is applied to DNA, and hence blocking can be eliminated.

Figure 18:
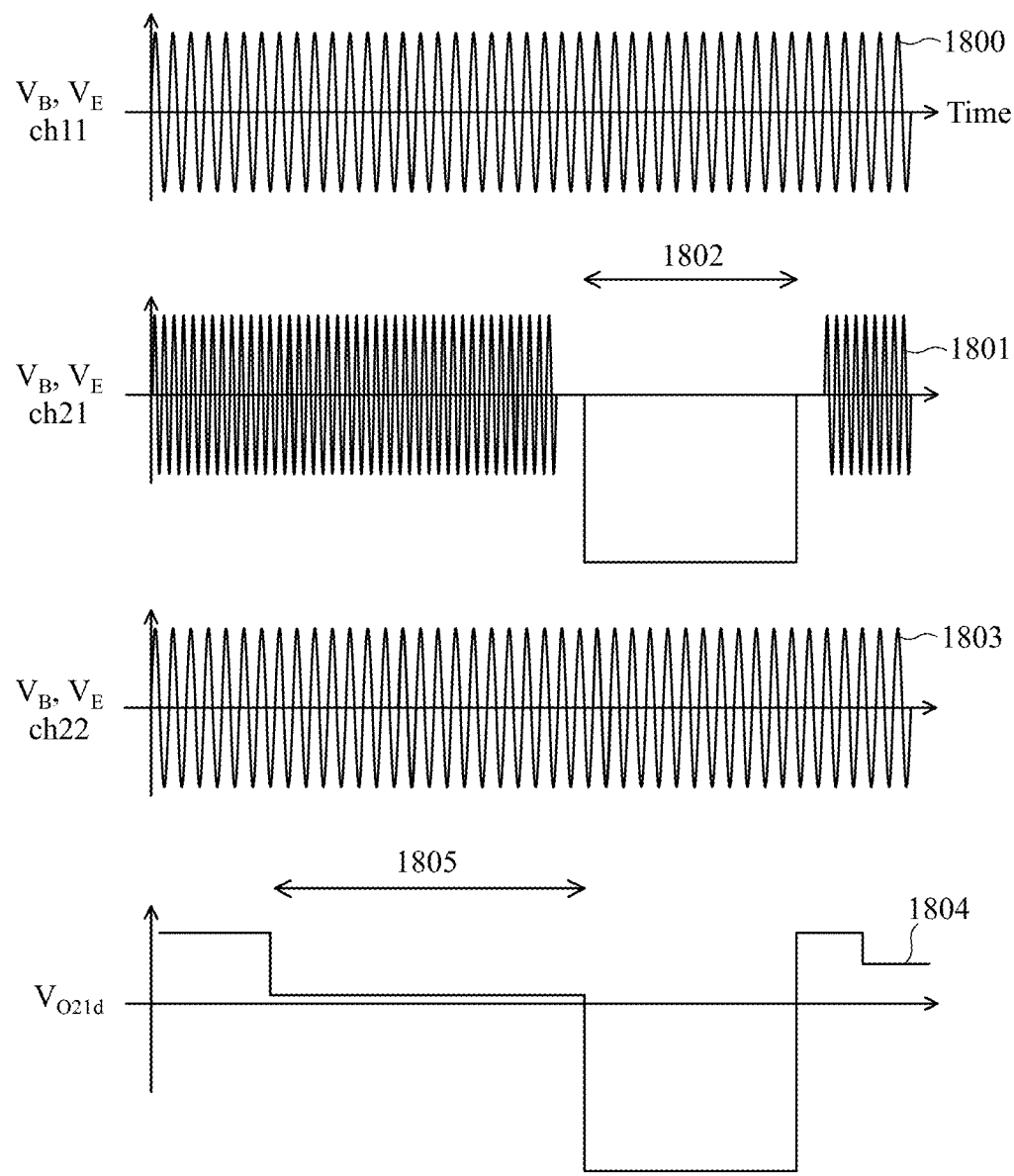
FIG. 18 is exemplary bias voltage waveforms at ch11, ch21, and ch22.

FIG. 18 shows exemplary bias voltage waveforms at ch11, ch21, and ch22. As apparent from bias voltage waveforms 1800 and 1801, in the normal measurement of the blockade current, channels ch11 and ch21 adjacent to each other are modulated at different frequencies to the bias voltage. A waveform 1804 is the waveform of a blockade current $V_{O21d}$ after an output signal $V_{O21}$ of ch21 is detected. When the nanopore 110 is blocked, the blockade current is stabilized at a low level as a waveform 1805 for a relatively long time. The arithmetic logic unit 405 determines whether the nanopore 110 has been blocked based on a threshold at a predetermined blockade current level and a threshold in stable time. In the case in which it is determined that the nanopore 110 has been blocked, the bias voltage is switched to $V_{ZAP}$ selectively for the nanopore that has been blocked by the switch 1601 through the control circuit 1600. The bias voltage $V_B$ is then greatly changed to the negative side as a waveform 1802. Consequently, a force in the direction reverse to the translocation direction is imparted to DNA, and hence the blocking of the nanopore 110 can be eliminated.

Since such operation of eliminating blocking sometimes causes a change in the voltage larger than signal fluctuations of the blockade current, this causes crosstalk between the adjacent channels. However, the channel adjacent to the channel that is subjected to the operation of eliminating blocking has modulated and demodulated blockade current signals. Thus, the influence of crosstalk due to the operation of eliminating blocking can be reduced. In the case in which the operation of eliminating blocking might cause the application of an unexpected overvoltage to the nanopore 110 in the adjacent channel to increase the pore diameter, the bias voltage of the adjacent channel may be fixed to a stand-by voltage $V_{STBY}$. Consequently, an increase in the pore diameter in the adjacent channel can be decreased.

<Exemplary Modifications of the Present Invention>

The present invention is not limited to the foregoing embodiments, which includes various exemplary modifications. For example, the foregoing embodiments are described in detail for easy understanding of the present invention, which are not necessarily limited to those including all the described configurations. A part of the configuration of an embodiment can be replaced by the configuration of another embodiment. The configuration of another embodiment can also be additionally provided on the configuration of an embodiment. Regarding parts of the configurations of the embodiments, the addition, removal, or replacement of other configurations can be made.

REFERENCE SIGNS LIST

101: reference chamber
102: first chamber
103: second chamber
104: reference electrode
105: electrolytic solution
106: first electrode
107: second electrode
108: nanopore chip
109: membrane
110: nanopore
114 to 115: ammeter
116 to 117: voltage source
120 to 124: partition wall
401: trans-impedance amplifier
402: differential amplifier
403: filter circuit
404: analog-to-digital converter
405: arithmetic logic unit
406: amplifier circuit
407: voltage source
701: analog mixer
702: filter
703: phase shifter
800: guard electrode
801: wire
900 to 901: voltage source
904 to 905: separate electrode
906: partition wall
1100: actuator
1101: substrate
1200: calibration circuit
1205: voltage source
1400: bias voltage selection switch
1401: drive timing control circuit
1600: control circuit
1601: switch

The invention claimed is:

1. A biomolecule measuring device that measures a biomolecule, comprising:
   a first chamber and a second chamber partitioned from each other with a partition wall;
   a first electrode that applies a voltage to a solution accommodated in the first chamber;
   a second electrode that applies a voltage to a solution accommodated in the second chamber;
   a reference chamber connected to the first chamber through a first hole of a thin film and the second chamber through a second hole of the thin film;
   a reference electrode that applies a voltage to a solution accommodated in the reference chamber; and
   a voltage applier that supplies a voltage to the first electrode and the second electrode,
   wherein
   the reference chamber communicates with the first chamber through the first hole of the thin film; and
   the reference chamber communicates with the second chamber through the second hole of the thin film, and
   wherein the voltage applier supplies the voltage to the first electrode and the voltage to the second electrode are modulated differently, and
   wherein the voltage applier supplies an alternating current voltage to the first electrode and to the second electrode, and
   wherein the alternating current voltage has a bias voltage offset from a voltage of the reference electrode.

2. The biomolecule measuring device according to claim 1,
   wherein the voltage applier supplies a voltage to the first electrode and the second electrode such that a first potential difference between a potential of the reference electrode and a potential of the first electrode and a second potential difference between the potential of the reference electrode and a potential of the second electrode are temporally divided.

3. The biomolecule measuring device according to claim 1, further comprising:
   an electric current measuring device that measures a first electric current flowing through the first electrode;
   an analog-to-digital (AD) converter that converts a measured result of the first electric current measured by the electric current measuring device into a digital value; and
   a control circuit that controls a timing of operating the AD converter,
   wherein the voltage applier stops a voltage supply to the first electrode in a time period which the voltage applier supplies a voltage to the second electrode, and
   wherein the control circuit stops the AD converter in a time period which the voltage applier supplies a voltage to the second electrode.

4. The biomolecule measuring device according to claim 1, further comprising:
   a wire that connects the voltage applier to the first electrode; and
   a guard electrode disposed along the wire,
   wherein the voltage applier supplies, to the guard electrode, a voltage identical to a voltage to be supplied to the first electrode.

5. The biomolecule measuring device according to claim 1, further comprising an electric current measuring device that measures a first electric current flowing through the first electrode,
   wherein in a time period which the electric current measuring device does not measure the first electric current, the voltage applier supplies, to the first electrode, a large voltage having an absolute value larger than an absolute value of a voltage supplied to the first electrode by the voltage applier in a time period which the electric current measuring device measures the first electric current.

6. The biomolecule measuring device according to claim 5,
   wherein in a time period which the voltage applier supplies the large voltage to the first electrode, the voltage applier supplies a fixed voltage to the second electrode.

7. The biomolecule measuring device according to claim 1,
wherein the voltage applier further includes a calibration circuit that applies a fixed voltage to the second electrode and switches for selecting a first mode in which an identical voltage is applied to the reference electrode and to the first electrode and for selecting a second mode in which a fixed voltage is applied to the reference electrode and an identical voltage is applied to the first electrode and to the second electrode, and
wherein the biomolecule measuring device further comprises an electric current measuring device that measures a first electric current flowing through the first electrode.

8. The biomolecule measuring device according to claim 7, further comprising an operating unit that calculates an electric current component flowing through the first hole based on a result measured by the electric current measuring device,
wherein the operating unit uses a result measured by the electric current measuring device in the first mode to calculate a parasitic capacitance between the first chamber and the second chamber, and uses a result measured by the electric current measuring device in the second mode to calculate a parasitic capacitance of the first chamber, and
wherein the operating unit uses the calculated parasitic capacitances to calculate an electric current component flowing through the first hole.

9. The biomolecule measuring device according to claim 8,
wherein after the first chamber, the second chamber, and the reference chamber are filled with an electrolytic solution, the voltage applier performs the first mode or the second mode.

10. The biomolecule measuring device according to claim 1, further comprising an actuator that moves the biomolecule.

* * * * *